United States Patent [19]
Eskelinen

[11] Patent Number: 5,349,963
[45] Date of Patent: Sep. 27, 1994

[54] METHOD AND APPARATUS FOR MEASURING MUSCLE FATIGUE

[75] Inventor: Paavo Eskelinen, Oulu, Finland
[73] Assignee: Sanhill Oy, Oulu, Finland
[21] Appl. No.: 103,749
[22] Filed: Aug. 6, 1993
[51] Int. Cl.$^5$ ............................................. A61B 5/0488
[52] U.S. Cl. ............................................... 128/733
[58] Field of Search .................... 128/733, 731–732

[56] References Cited
U.S. PATENT DOCUMENTS

| | | | |
|---|---|---|---|
| 3,641,993 | 2/1972 | Gaarder et al. | 128/733 |
| 4,213,467 | 7/1980 | Stulen et al. | 128/733 |
| 4,592,369 | 6/1986 | Davis et al. | 128/733 |

*Primary Examiner*—Angela D. Sykes
*Attorney, Agent, or Firm*—Ladas & Parry

[57] ABSTRACT

A method and an apparatus for measuring muscle fatigue is disclosed, in which electromyographic (EMG) signals are measured from a muscle in order to determine the fatigue level of the muscle. The invention comprises the steps of: receiving an EMG input signal from electrodes attached to the muscle to be analyzed; sampling said input signal to a sequence of discrete signal values; calculating the difference between several pairs of successive sample values; depending on the sign of the calculated difference, adding cumulatively the sampled values in a first or second accumulator means, and said difference values in a third accumulator means; obtaining separate sequences of quotients between the values representative of the output from said third accumulator means and values representative of the outputs from said first and second accumulator means, respectively; obtaining for each of said sequences a single quotient having a weighted value representative of a number of said quotients; multiplying the obtained weighted values with each other in order to obtain an index indicative of fatigue during said time period in said muscle.

14 Claims, 3 Drawing Sheets

METHOD AND APPARATUS FOR MEASURING MUSCLE FATIGUE

BACKGROUND OF THE INVENTION

1. Field of the Invention

The present invention relates to a method and an apparatus for measuring muscle fatigue, in which electromyographic (EMG) signals measured from a muscle are used to determine the fatigue level of the muscle.

2. Description of Prior Art

There are two basic methods to assess muscle fatigue: mechanical and electrical. Mechanical methods are based on measuring direct force output from muscle performance. This is, however, mostly unpractical and unreliable due to inability to separate each muscle component force from the total output force. Muscular systems have a strong tendency of compensating weak muscles with stronger ones in a constant dynamic fashion. In practice, by measuring single muscular contraction indirectly through muscle electrical signals (EMG), more precise conclusions can be drawn about the neurophysiological status of the muscle. Consequently, it has become widely accepted to deploy certain signal processing methods for EMG to gain information about muscle fatigue. In the following, a first exemplary technique to be discussed is based on estimation of spectral parameters, and a second technique to be discussed uses simple time domain signal processing.

In the first case, a measure of some form of average frequency (spectral shift) is calculated through the signal (EMG) spectrum. The original signal is sampled to produce a discrete time series, which is then subdivided into shorter segments of N samples each. For each segment spectral components (Fourier Spectrum) are estimated exploiting commonly known Fast Fourier Transform (FFT) algorithms. Average frequency calculations normally resort to power spectrum, which can be readily derived from the original Fourier spectrum. The two most popular frequency parameters used as fatigue descriptors are Mean Power Frequency (MPF) and Median Frequency (MF).

The second technique, called Zero Crossings (ZC), is a strongly simplified way of estimating average signal frequency in time domain, although it can be also defined through spectral calculations. Average intensity of rectified and smoothed EMG signal has also been correlated to some extent with muscle fatigue, but this has not gained as much popularity as the two other techniques.

In discrete form the two spectral parameters can be written by $$MPF = \frac{\sum_{0}^{N-1} f_k P(f_k)}{\sum_{0}^{N-1} P(f_k)} \quad (1)$$

$$\sum_{0}^{MF} P(f_k) = \sum_{MF}^{N-1} P(f_k) \quad (2)$$

In the second technique (ZC) the time domain approach simply tries to determine the number of polarity changes in the signal during a given period of time.

$$ZC = \Sigma hd\ j[s(\Gamma)_j + s(\mathrm{L})_j] \quad (3)$$

where $s(\Gamma)_j$ denotes the $j^{th}$ polarity change of the signal from negative to positive; and $s(\mathrm{L})_j$ denotes the $j^{th}$ polarity change from positive to negative.

As mentioned earlier, there are ways of estimating ZC rates through spectral calculations, but they are rarely used due to slower processing times and inherent uncertanties as compared to direct time domain estimations.

Several problems emerge as these methods are applied to assess fatigue reflected in EMG signals. To achieve fast spectral estimations FFT algorithms are commonly used. This implies limiting the source time series segment to specific number of points, i.e. only groups of points having $2^N$ elements (N is a positive integer) can be processed by FFT.

It has been suggested different solutions to circumvent these problems, but basically only few different size groups of points are allowed. This means that a huge number of varying length signal segments cannot be analyzed directly by FFT. The only known method to manage arbitrary number of points is the actual Discrete Fourier Transforms which is unpractical because of the much greater number of calculations required compared to FFT.

The basic problems with spectral estimations are, however, intrinsic. First of all, power spectrum is not unique. There is an unlimited number of different signals that can produce exactly the same power spectrum. Secondly, varying amounts of errors are always introduced to spectral estimations due to the finite number of temporal points and also due to different windowing functions used. Thirdly, the Fourier spectrum implies sinusoidal structural model for its target, which is rarely the case in physiological signals. These three factors to large extent can be credited to great amount of unspecificity and insensitivity found in many physiological signal analysis applications using spectral estimators.

Zero crossings methodology, on the other hand, does not account for any other information except the signal polarity. Therefore, any signal behaviour between two consequtive polarity changes will be left unnoticed. Since signal changes are mostly unpredictable in e.g. EMG, huge ammounts of information are ignored by using the ZC analysis method.

OBJECT OF THE INVENTION

The object of the present invention is to provide a reliable index for determination of muscle fatigue. More specifically, an object is to provide a muscle fatigue measuring method based on a discrete sampling technique, due to the greater amount of flexibility of digital electronics compared to analogue circuitry in signal processing.

DETAILED DESCRIPTION OF PREFERRED EMBODIMENTS

Figure 1:
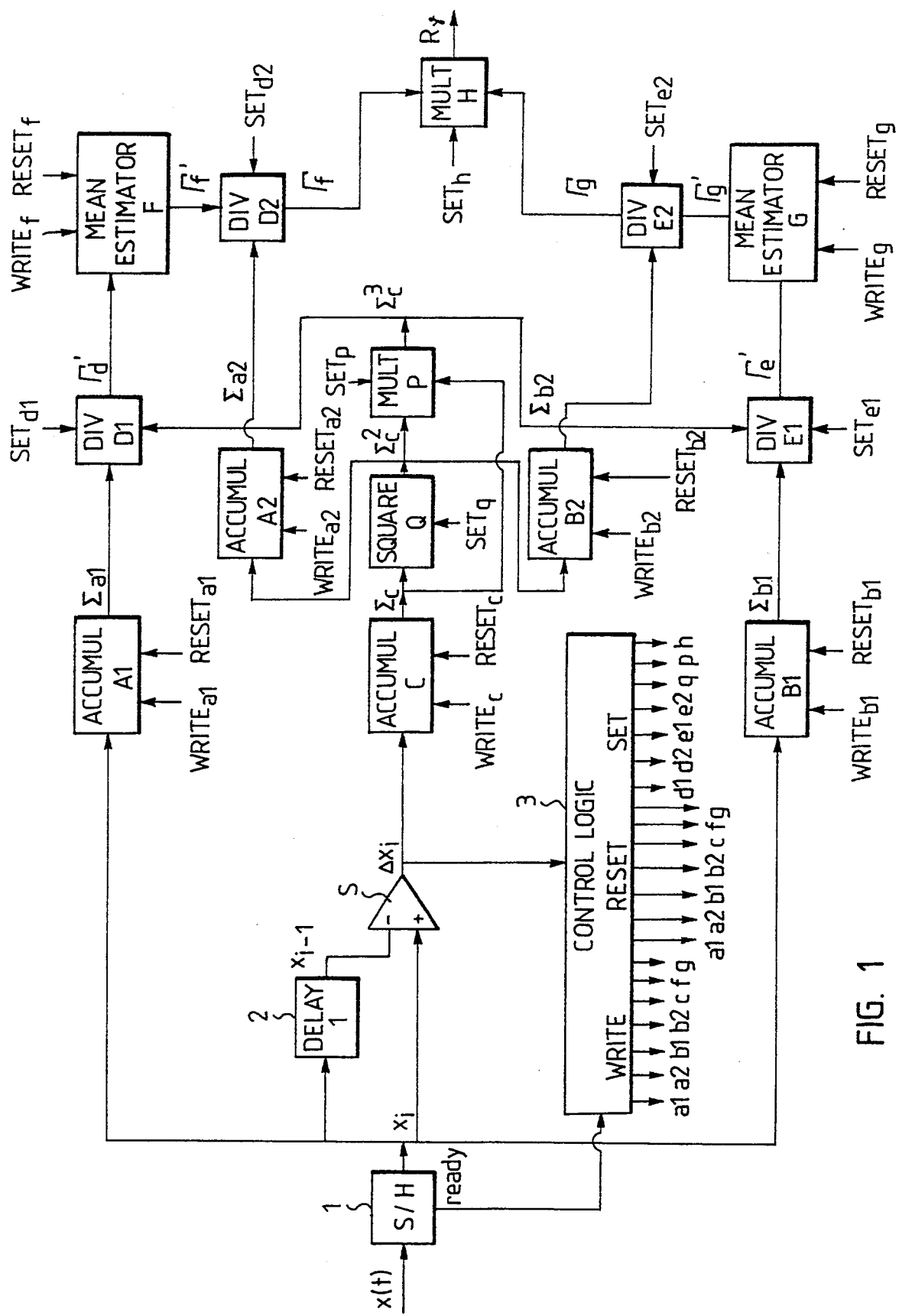
FIG. 1 shows an apparatus according to the present invention for measuring muscle fatigue

The inventive system approach to provide a more reliable index for quantification of muscle fatigue is shown in FIG. 1. This system model is based on a discrete approach instead of a continuous one, due to greater amount of flexibility of digital electronics compared to analogue circuitry in signal processing.

The input signal x(t), which is the actual EMG signal derived from electrodes, is sampled and held stable by a S/H unit 1. The sampled value of $x_i = x(t)|_{t=ti}$ is then fed into four separate system units: accumulator A1, accumulator B1, delay circuit 2 and the positive input of a subtraction unit S. Both delay circuit 2 and subtraction unit S are receiving each of the sampled values $x_i$, but input values to accumulators A1 and B1 are selectively written to these units. Whether or not a particular value $x_i$ is written to either one of these accumulators is decided by the control logic circuit 3, as will be explained in connection with FIG. 2.

Each value of the difference $\Delta x_i$ of two consequtive values $x_i$ and $x_{i-1}$ is written to accumulator C. The output signal of accumulator C is fed to a squaring unit Q and a multiplier unit P for further processing, which will be explained later.

Generally, the cumulative output signals of the accumulators are hereinafter referred to by a sigma character accompanied by an appropriate subindex, i.e. the output signal of accumulator C is denoted $\Sigma_c$. The output of accumulator C is further processed to produce both the square and cube values of $\Sigma_c$. These will constitute a weighing function for the output values, in order to emphasize larger changes in the signal. Accumulators A2 and B2 will perform the neccessary scaling for this procedure, as they receive as an input signal a squared value of the output $\Sigma_c$ of accumulator C. It is obvious that other kinds of weighing functions can be applied. Any writing operation to these accumulators is supervised by the control logic circuit 3.

All five accumulators are reset to zero from time to time by the Control Logic, which derives the reset criteria from one input signal the $\Delta x_i$.

After that a number of $x_i$ samples have been received, the accrued values at the accumulator outputs are processed by two divider units D1 and E1. As certain criteria (explained later) in the control logic 3 becomes valid, the control logic signals $SET_q$, $SET_p$, $WRITE_{a2}$ or $WRITE_{b2}$ as well as $SET_{d1}$ or $SET_{e1}$ activate the corresponding divider units resulting in new divider output values (quotients) $\Gamma'_d$ or $\Gamma'_e$, respectively. An example of how this values are calculated, we have $$\Gamma'_e = (\Sigma_c)^3/\Sigma_{b1} \tag{4}$$

This value is immediately written to a pertinent mean estimator unit F or G. For example, the mean estimation process may simply consist of taking the arithmetic mean, i.e. average, of a sequence of input values $\Gamma'_d$ or $\Gamma'_e$:

$$\Gamma'_{gk} = \frac{1}{M} \sum_{0}^{M-1} \Gamma'_{ej}, \text{ where } k = 0, 1, 2, \ldots \tag{5}$$

Another model for the mean estimator would be to compute the median values.

Finally, for each new pair of $(\Gamma'_f, \Gamma'_g)$, the control logic issues the $SET_{d2}$ and $SET_{e2}$ signals in order to activate second divider units D2 and E2. This will result in the following output values from D2 and E2:

$$\Gamma_f = \Gamma'_f/\Sigma_{a2} \tag{6}$$

-continued $$\Gamma_g = \Gamma'_g/\Sigma_{b2}$$

After this, a $SET_h$ command will be issued in order to activate the multiplier unit H. The output of this unit constitutes the actual analysis result in the form of a time series:

$$R_{65k} = \Gamma_{fk} \cdot \Gamma_{gk}, \text{ where } k = 0, 1, 2, \ldots \tag{7}$$

The values of $R_{65}$ tend to decrease as muscle fatigue increases. Examples on this phenomenon are shown later in the text.

Figure 2:
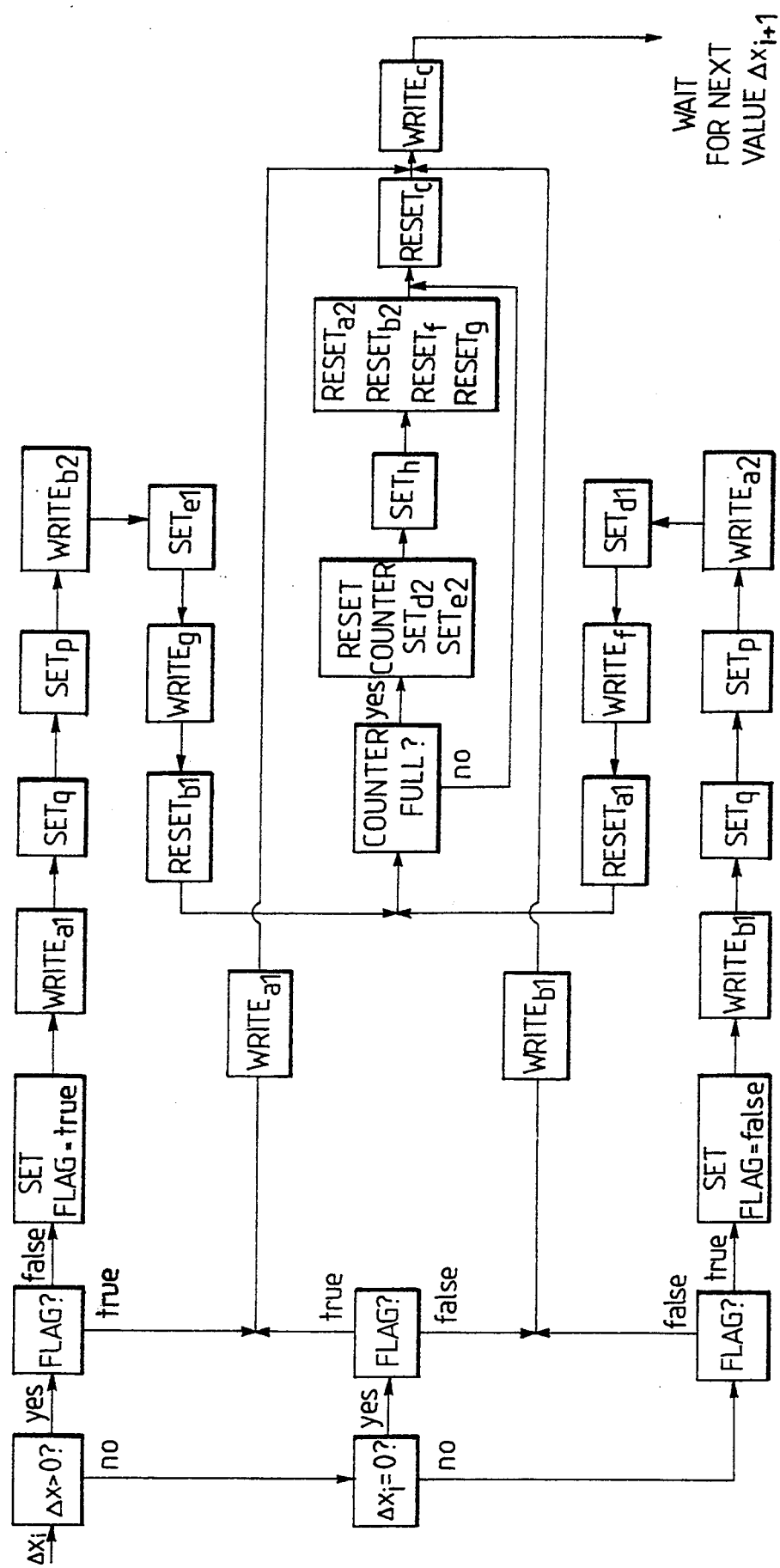
FIG. 2 shows a decision flowchart of the control logic unit of FIG. 1.

Referring now to FIGS. 1 and 2, a detailed description of the operation of control logic unit 3 is given.

There is only one input to the unit: $\Delta x_i$. At an initial stage as sampling is to be started, FLAG will be set according to the difference of the first two values available, i.e. $x_1 - x_0$. If the difference proves to be zero, then the next possible difference will be tested: $x_2 - x_1$. This testing of differences will be continued until a nonzero difference is detected, in which case FLAG will be set to TRUE, if the difference is positive, and to FALSE if the difference is negative.

In FIG. 2, a continuous process is shown where the $i^{th}$ $\Delta x$ value $\Delta x_i$ is processed, whereby the initial FLAG value has been set earlier. In this continuous process, $\Delta x_i$ is first checked for positive values. If this value appears positive, then FLAG is tested. If it is TRUE, it means that the signal is still growing in value, and only two actions will follow: the current value of $x_i$ will be written to accumulator A1 and the current value of $\Delta x_i$ will be written to accumulator C.

If FLAG turns out to be FALSE, a series of actions will follow. This is a critical point of the inventive method, because now a change in the signal direction has occured, which means that the derivative of the input signal has changed its sign. In this specific case, the signal has now started to decrease in value instead of growing. This activates the control unit in a number of different ways, resulting in the calculation of new values to be presented at the outputs of the various calculation means, as will be explained in the following.

Depending on which way the change has become actual, whether it has been altered from growing to decreasing or vica versa, a different series of control actions will be realized. If $\Delta x_i$ is positive, then the FLAG, having been false, will be immediately set to TRUE and the value $x_i$ is written to accumulator A1. Immediately following this, a $SET_q$ signal is issued, followed by a $SET_p$ signal, allowing the squaring unit Q and the multiplier unit P to produce the square and cube, respectively, of the accumulator C output signal. Next the square value is written to accumulator B2 and a $SET_{e1}$ signal is issued in order to activate the divider unit E1. Now a new value of $\Gamma'_e$ can be read at the output of E1, which value is written to the mean estimator G by a $WRITE_g$ procedure. This is followed by a $RESET_{b1}$ signal to clear accumulator B1 and prepare it for the next accumulative process.

The control logic unit 3 includes counter means to synchronise the two mean estimators F and G. This can be done in several ways, for example the counter can be used to count a fixed time period, for which one analysis result would be produced or by incrementing the corresponding counter by one every time a new value is written to a mean estimator. Now e.g. in the first case the FULL value of the counter would indicate how many samples (N) are to be acquired, before a new value of $R_{65}$ would be estimated.

As the counter reaches the FULL condition, it will be reset to its initial value, and $SET_{d2}$ and $SET_{e2}$ commands will be issued to produce a pair of values $(\Gamma_f, \Gamma_g)$ at the outputs of divider units D2 and E2. These values will be multiplied by multiplying unit H after the $SET_h$ command has been issued. The final output $R_{65}$ will now contain information about fatigue status of the muscle being analysed.

After the completion of one estimation and accumulation process cycle as described above, mean estimators F and G will be reset by signals $RESET_f$ and $RESET_g$, respectively. Accumulators A2, B2 and C will be reset by the respective signals $RESET_{a2}$, $RESET_{b2}$ and $RESET_c$. These actions will reset the contents of the mean estimators and accumulators to zero and commence a new mean estimation and accumulation process with no values written to these units at this point.

The case when $\Delta x_i = 0$ will also result in writing the value to accumulator C and, depending on the FLAG status, to either of accumulators A1 or B1.

As can be seen from FIG. 2, there is a symmetric flow of events for the two cases $\Delta x_i > 0$ and $\Delta x_i < 0$. Therefore, the explanation of the control flow in the latter case is analogous to the first one.

After the control logic 3 has performed all neccessary functions, it will start waiting for the next value $\Delta x_{i+1}$, which is provided by the sample&hold unit 1 of FIG. 1.

Figure 3:
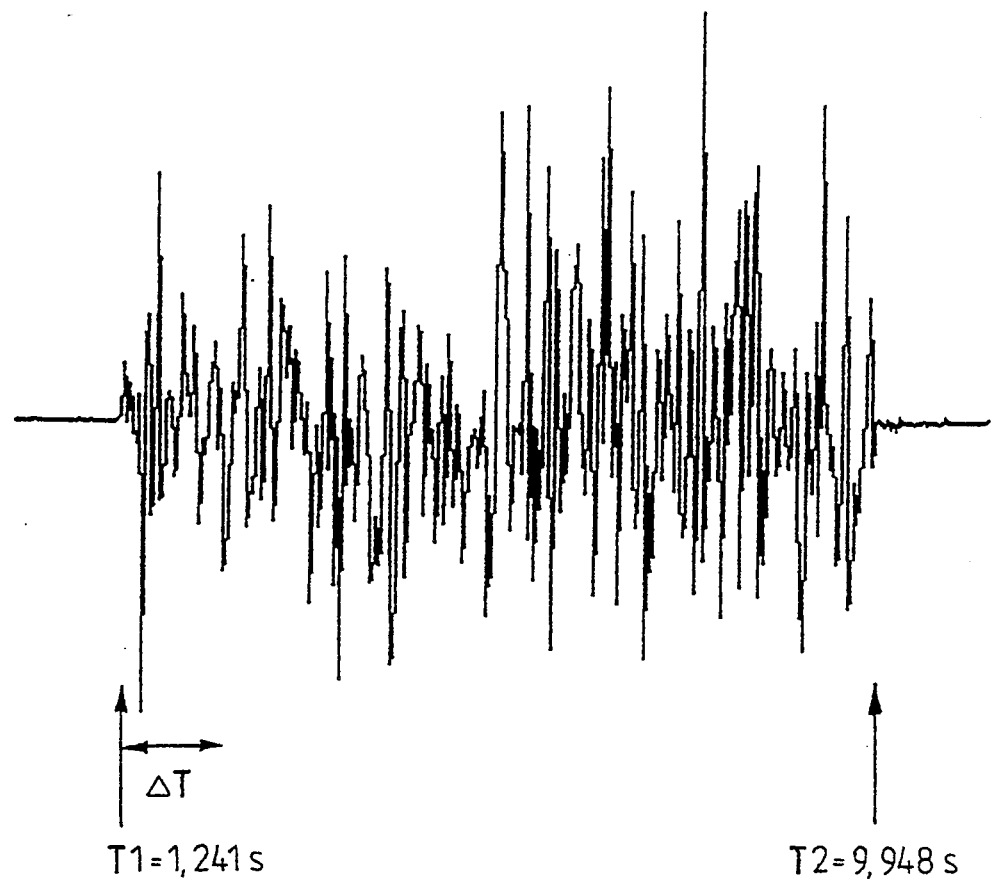
FIG. 3 shows a typical EMG signal segment.
Figure 4:
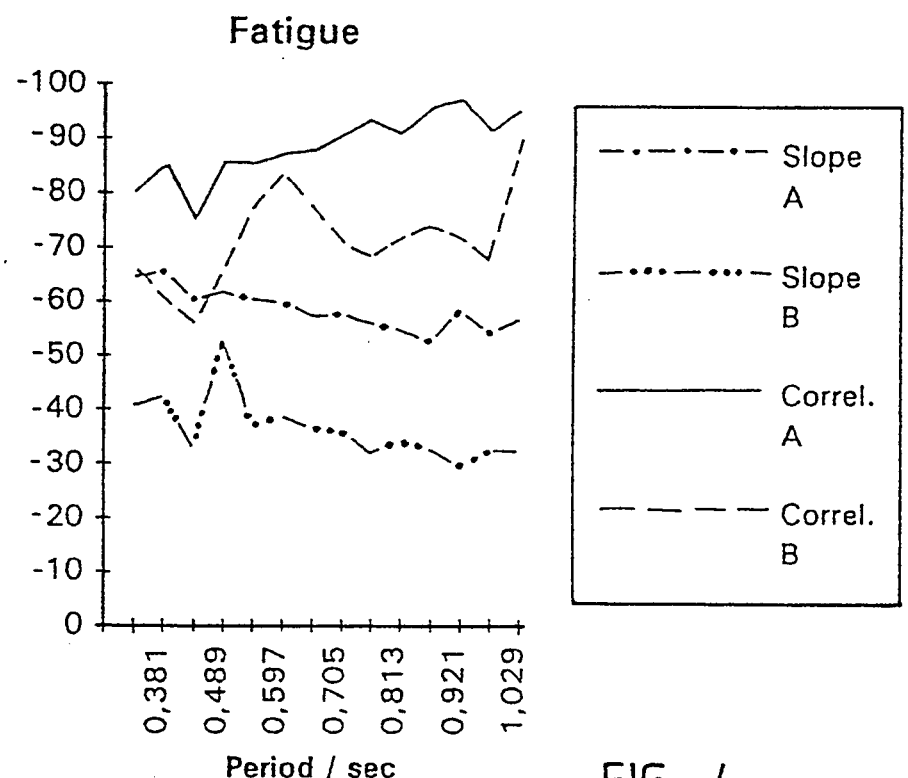
FIG. 4 shows data from an analysed signal according to FIG. 3.

Referring now to FIGS. 3 and 4, an EMG (electromyography) signal segment shown in FIG. 3 can be analysed in the following manner:

Between a starting point T1 and an end point T2, the signal has been subdivided into equal length periods of time ($\Delta T$). According to FIG. 4, the first analysis subsegment has been chosen to be 327 ms, which equals 654 sampled values of EMG. The starting point T1 has been set to T1=1.241 s, at which time onset of EMG activity occurs. The end point has been set to T2=9.948 s, at which time there is a rapid diminishing intensity of the EMG signal.

Each subsegment (period) has been analysed to yield two distinct signal descriptors: conventional MF (Median Frequency) and the new descriptor derived by the method accordding to the present invention, the $R_\gamma$. Analysis of the consecutive periods yields two separate discrete time series of these two descriptors. The two series are then submitted to least squares linear fit analysis producing an estimate for the slope of each series together with the correlation coefficient. Table 1 and FIG. 4 exhibits Slope A for the $R_{65}$ series and Slope B for the MF series. Both series have been normalised relative to 100. The corresponding correlation coefficients as percentages are listed by Correl. A and Correl. B.

TABLE 1

| | Period/s | Slope A | Slope B | Corr. A | Corr. B |
|---|---|---|---|---|---|
| T1 = 1.241 s | 0.327 | −64.40 | −40.60 | −80.00 | −66.60 |
| T2 = 9.948 s | 0.381 | −65.40 | −42.30 | −84.90 | −60.50 |
| | 0.435 | −60.20 | −32.90 | −74.70 | −55.50 |
| | 0.489 | −61.60 | −52.40 | −85.50 | −65.70 |
| | 0.543 | −60.20 | −36.90 | −85.10 | −77.20 |
| | 0.597 | −59.70 | −38.40 | −86.90 | −83.50 |
| | 0.651 | −57.50 | −36.50 | −87.90 | −77.10 |
| | 0.705 | −57.60 | −35.80 | −90.40 | −71.10 |
| | 0.759 | −55.90 | −32.10 | −93.30 | −68.10 |
| | 0.813 | −54.70 | −34.30 | −90.90 | −71.60 |

TABLE 1-continued

| | Period/s | Slope A | Slope B | Corr. A | Corr. B |
|---|---|---|---|---|---|
| | 0.867 | −52.40 | −32.40 | −95.40 | −73.60 |
| | 0.921 | −58.10 | −29.30 | −97.30 | −71.70 |
| | 0.975 | −54.30 | −32.40 | −90.90 | −66.90 |
| | 1.029 | −56.50 | −32.20 | −95.70 | −88.90 |
| Median | −57.85 | −35.05 | −89.15 | −71.35 | |
| Average | −58.46 | −36.32 | −88.49 | −71.29 | |
| Average dev | | ±2.96 | ±4.17 | ±4.92 | ±6.37 |
| Stand. dev | | ±3.73 | ±5.87 | ±6.29 | ±8.69 |

The slope is an estimate of the intensity of the muscle fatiguing process. The steeper the slope the more fatigue is evident in the muscle concerned. If the muscle is subjected to rehabilitation then—provided the treatment proves effective—successive measurements during the treatment phase should produce increasing slope values.

The signal has been registered through standard surface electrodes from musculus flexor carpi ulnaris during maximal isometric contraction. This experiment was chosen to be most favourable to conventional fatigue analysis methodology, and particularly in this case to MF analysis. It is well known that as muscular fatigue increases, MF of the muscle EMG signal decreases almost in a linear fashion.

Normally only one value for the period length is applied, but in this example the period has been given several values to overcome any statistical bias attached to one value periods. From FIG. 4 it is clear that as the period length is increased, the estimate of the slopes tends to decrease in both cases. This is probably due to stronger averaging effect in longer periods. Also interestingly, correlation coefficients approach 100% as the period length is increased.

The graphs in FIG. 4 (Fatigue 1) show that the MF change is clearly more insensitive to the fatiguing phenomenon than the $R_{65}$ variation (absolute value of the normalised slope) and, furthermore, the MF graph displays more statistical fluctuations as a function of different analysis period lengths. The latter can be partly contributed to the fact that as period lengths are changed, the FFT algorithms are not always able to utilise all subsegment data values as one single group. The new and inventive methodology has no such limitations, and the $R_\gamma$ slope behaves statistically very smoothly with increasing period lengths.

The correlation coefficient for the MF technique depicts also intense variability with different subsegment lengths. Statistically this carries severe implications for a methodological source of errors in estimating muscle fatigue. As for the method according to the present invention, correlation coefficients form a well behaving, almost monotonic function, which again demonstrates its high degree of statistical stability. The correlation coefficients are also higher for the $R_{65}$ slopes than for the MF ones.

These differences in statistics can also be verified numerically by the overall statistics of the four series in Table 1.

Relative average deviation of the MF slope is 11.5%, relative standard error is 4.3%—for the corresponding correlation coefficient these figures are 9.0% and 3.3%. For the $R_{65}$ method these values turn out to be: relative average deviation of the slope: 5.1%, relative standard error 1.7%. Similarly for the correlation coefficient:

relative average deviation 5.6% and relative standard error 1.9%.

The MF technique produces in the case of the slope uncertainties more than twice greater than those inherent in the method according to the present invention, and correlation coefficient variability for the MF technique appears almost twice as great as in the $R_\gamma$ case.

This multivalue period analysis is highly suitable for the new inventive methodology, because all subsegment data samples can always be included in the analysis process. This approach is also more reliable than the one value case; analysis dependencies on period length can be effectively eliminated.

Finally, a fixed period length was chosen to allow the MF algorithms to exploit all subsegment samples (period with 1024 data values.) This number of samples was chosen because for this particular setup, MF seemed to produce good correlation. The two methods were now compared by scanning through all subsegments ten times. Each time a new scan was performed, the starting point T1 was slightly shifted forward by 52 ms, but the subsegment length remained the same. In practice, as far as muscle fatigue is concerned, all the scans were analysing the same overall time segment T1 ... T2. The achieved results, together with differences in percentage betweeen the two methods are shown in table 2:

TABLE 2

| | | |
|---|---|---|
| Slope A | Mean: −58.1 | Standard error: 1,4% |
| Slope B | Mean: −38.3 | Standard error: 2,5% (+78%) |
| Corr. coeff. A | Mean: −88.1 | Standard error: 0.6% |
| Corr. coeff. B | Mean: −82.3 | Standard error: 1.5% (+250%) |

Again, the same pattern of the differences in sensitivity to fatigue and its correlation coefficient as well as the degree of statistical uncertainties can be distinguished.

It is obvious to one skilled in the art that the present invention is not confined to the examples described above, but that various embodiments of the invention may vary within the scope of the attaced claims.

I claim:

1. A method for measuring muscle fatigue, in which electromyographic (EMG) signals measured from a muscle are used to determine the fatigue level of the muscle, the method comprising the steps of:

receiving an EMG input signal x(t) from electrodes attached to the muscle to be analyzed;

sampling said input signal to form a sequence of discrete signal values $x_i$;

calculating the difference $\Delta x_i$ between several pairs of successive sample values $x_i$ and $x_{i-1}$;

depending on the signal of the calculated difference $\Delta_{xi}$, adding cumulatively the sampled values $x_i$ in a first accumulator means (A1) if said difference is positive, and in a second accumulator means (B1) if said difference is negative, and said difference values $\Delta_{xi}$ in a third accumulator means (C);

obtaining separate sequences of quotients between the values representative of the output from said third accumulator means and values representative of the outputs from said first and second accumulator means, respectively;

obtaining for each of said sequences a single quotient having a weighted value representative of a number of said quotients; and multiplying the obtained weighted values with each other in order to obtain an index indicative of fatigue in said muscle.

2. Method according to claim 1, including performing the cumulative addition of the sampled values $x_i$ to said first, second and third accumulator means in a cyclic fashion for a number of sample values, after which the sums of the accumulator means are read and the accumulator means are reset.

3. Method according to claim 1, wherein the step of obtaining separate sequences of quotients id done in a cyclic fashion with a predetermined number of quotients, performing a statistical analysis of the quotients after at least one sequence containing a predetermined number of quotients has been provided, whereafter the resulting value is read and new quotients sequences are generated.

4. Method according to claim 1, wherein the single weighted quotient value for each of said sequences is obtained by calculating the arithmetic mean of the quotients.

5. Method according to claim 1, wherein the single weighted quotient value for each of said sequences is obtained by calculating the median value of the quotients.

6. Method according to claim 1, including the steps of further processing the output values of said third accumulator means by producing the square and cube values of said output values of said third accumulator means, which provide a scaled emphasis function for said output values ($\Sigma_c$).

7. Method according to claim 6, including the steps of further dividing the weighted quotient values with a second value representative of the square of the output from said third accumulator means; and multiplying the obtained values with each other in order to obtain an index indicative of fatigue during said time period in said muscle.

8. Apparatus for measuring muscle fatigue, in which electromyographic (EMG) signals from a muscle are measured to determine the fatigue level of the muscle, the apparatus comprising:

input means (1) adapted to receive an EMG input signal x(t) from electrodes attached to the muscle to be analyzed and to sample said input signal to form a sequence of discrete signal values $x_i$;

difference calculating means (S) for computing the difference $\Delta x_i$ between several pairs of successive sample values $x_i$ and $x_{i-1}$;

control logic means (3) for determining the sign of said difference $\Delta x_i$ and for providing the signals necessary for controlling the EMG measuring apparatus;

first, second and third accumulator means (A1, B1, C) for selectively receiving, depending on the sign of the calculated difference $\Delta x_i$, sampled values $x_i$ and said difference values $\Delta x_i$;

dividing means (D1, E1) for computing separate sequences of quotients between values representative of the output from said third accumulator means and values representative of the output from one of said first and second accumulator means, respectively;

statistical analyzing means (F,G) for obtaining for each of said sequences a single weighted quotient value representative of a number of said quotients; and multiplying means (H) for multiplying the obtained weighted values with each other in order to obtain an index indicative of fatigue during said time period in said muscle.

9. Apparatus according to claim 8, wherein each of the said accumulator means includes a reset input terminal which receives an reset signal when a predetermined number of sample values $x_i$ have been cumulatively added and calculated upon.

10. Apparatus according to claim 8, wherein the statistical analyzing means (F,G) includes a reset input terminal which receives a reset signal when said predetermined number of said quotients on each sequence of quotients have been statistically calculated upon.

11. Apparatus according to claim 8, wherein the statistical analyzing means (F,G) comprises means for calculating the arithmetic mean of the quotients.

12. Apparatus according to claim 8, wherein the statistical analyzing means (F,G) comprises means for calculating the median value of the quotients.

13. Apparatus according to claim 8, including processing means (Q, P) to produce the square and cube values of the output of said third accumulator means, which provides an emphasize function for the output values ($\Sigma_c$), and further accumulator means (A2, B2) which perform a necessary scaling operation to the emphasize function.

14. Apparatus according to claim 13, the apparatus further including second dividing means (D2, E2) for dividing the weighted quotient values with a second value representative of the square of the output from said third accumulator means.

* * * * *